US 10,179,735 B2

(12) United States Patent
Mautner

(10) Patent No.: US 10,179,735 B2
(45) Date of Patent: Jan. 15, 2019

(54) METHOD FOR PURIFYING CONTAMINATED GASEOUS HYDROGEN CHLORIDE

(71) Applicant: Wacker Chemie AG, Munich (DE)

(72) Inventor: Konrad Mautner, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/527,141

(22) PCT Filed: Jan. 26, 2016

(86) PCT No.: PCT/EP2016/051606
§ 371 (c)(1),
(2) Date: May 16, 2017

(87) PCT Pub. No.: WO2016/120288
PCT Pub. Date: Aug. 4, 2016

(65) Prior Publication Data
US 2018/0016141 A1   Jan. 18, 2018

(30) Foreign Application Priority Data

Jan. 28, 2015   (DE) .......................... 10 2015 201 446

(51) Int. Cl.
| | |
|---|---|
| *C01B 7/07* | (2006.01) |
| *C08G 77/32* | (2006.01) |
| *C08G 77/06* | (2006.01) |
| *C08G 77/34* | (2006.01) |
| *C08G 77/36* | (2006.01) |
| *C07C 17/16* | (2006.01) |

(52) U.S. Cl.
CPC .......... *C01B 7/0706* (2013.01); *C01B 7/0712* (2013.01); *C01B 7/0718* (2013.01); *C01B 7/0725* (2013.01); *C01B 7/0731* (2013.01); *C07C 17/16* (2013.01); *C08G 77/06* (2013.01); *C08G 77/32* (2013.01); *C08G 77/34* (2013.01); *C08G 77/36* (2013.01); *C01B 2210/0003* (2013.01)

(58) Field of Classification Search
CPC ..... C01B 7/0706–7/0737; C08G 77/06; C08G 77/32; C08G 77/34; C08G 77/36
See application file for complete search history.

(56) References Cited

U.S. PATENT DOCUMENTS

| | | | |
|---|---|---|---|
| 4,935,220 A | 6/1990 | Schneider et al. | |
| 2008/0287716 A1 | 11/2008 | Kaeppler et al. | |

FOREIGN PATENT DOCUMENTS

| | | |
|---|---|---|
| CN | 101306976 A | 11/2008 |
| CN | 101423193 A | 5/2009 |
| CN | 102250132 A | 11/2011 |
| CN | 203333289 U | 12/2013 |
| CN | 103724367 A | 4/2014 |
| CN | 103910332 A | 7/2014 |
| CN | 104058370 A | 9/2014 |
| DE | 3816783 A1 | 11/1989 |
| EP | 0342521 A1 | 11/1989 |
| JP | 5330804 A2 | 12/1993 |

*Primary Examiner* — Medhanit W Bahta
(74) *Attorney, Agent, or Firm* — Brooks Kushman P.C.

(57) ABSTRACT

Impure gaseous hydrogen chloride from organochlorosilane hydrolysis is freed of impurities by first scrubbing with an organochlorosilane, which may be the same or different from the organochlorosilane(s) hydrolyzed, and then further scrubbing with chloromethane. The purified gaseous hydrogen chloride is preferably used in chlorosilane synthesis.

11 Claims, No Drawings

METHOD FOR PURIFYING CONTAMINATED GASEOUS HYDROGEN CHLORIDE

CROSS REFERENCE TO RELATED APPLICATIONS

This application is the U.S. National Phase of PCT Appln. No. PCT/EP2016/051606 filed Jan. 26, 2016, which claims priority to German Application No. 10 2015 201 446.0 filed Jan. 28, 2015, the disclosures of which are incorporated in their entirety by reference herein.

BACKGROUND OF THE INVENTION

1. Field of the Invention

The invention relates to a process for purifying contaminated gaseous hydrogen chloride using liquid organochlorosilane.

2. Description of the Related Art

Organochlorosilane hydrolyses are frequently carried out in the industry in such a way that gaseous hydrogen chloride is formed. This hydrogen chloride usually contains not only moisture but also traces of starting silane and hydrolysis products thereof. In the case of dimethyldichlorosilane as a starting silane, traces of cyclic siloxanes, e.g. hexamethylcyclotrisiloxane and octamethylcyclotetrasiloxane, linear oligosiloxanes, e.g. dichlorotetramethyldisiloxane or dihydroxytetramethyldisiloxane and higher terminally chlorine- or hydroxy-substituted homologues, are present in addition to water.

The hydrogen chloride is, for example, used together with methanol in siloxane plants to produce chloromethane: MeOH+HCl-->MeCl+H$_2$O (Me=methyl).

If these siloxane constituents get into a chloromethane plant, then in the case of gas-phase catalysts, usually activated aluminum oxides, the catalyst becomes inactive due to covering of the surface. In the case of liquid-phase catalysis, it can lead to fouling in heat exchangers and the siloxane constituents go together with the water of reaction into the wastewater and there lead to CSB pollution.

For this reason, the hydrogen chloride is preferably free of silane and siloxane constituents before chloromethane production.

DE 3816783A1 describes the purification of contaminated hydrogen chloride by distillation. This is very complicated since, owing to its very low boiling point, hydrogen chloride has to be compressed in order to be able to condense the purified hydrogen chloride.

CN 101423193 A and CN 203333289 describe a scrub using cold hydrochloric acid, which preferably originates from the hydrolysis process. However, the hydrochloric acid has to be, for this purpose, cooled to temperatures below −15° C. by means of additional, technical apparatuses.

CN103724367A describes a scrub using chloromethane as part of a complex purification system. The low temperatures indicated incur the risk of icing by water and/or the presence of solid siloxane constituents; for example, the freezing point of octamethylcyclotetrasiloxane is 17-18° C. In the presence of moisture, corrosion-resistant materials are necessary for very low temperatures (<−40° C.), which greatly complicates the selection of material.

SUMMARY OF THE INVENTION

The invention provides a process for purifying contaminated gaseous hydrogen chloride containing impurities selected from among water, organochlorosilane A and hydrolysis products thereof, wherein the gaseous hydrogen chloride is scrubbed with liquid organochlorosilane B.

DETAILED DESCRIPTION OF THE PREFERRED EMBODIMENTS

The process is simple and inexpensive to carry out. The impurities are reliably removed. During handling of the scrubbed gaseous hydrogen chloride, there is no risk of icing; it is possible to use the materials customary for the handling of dry gaseous hydrogen chloride and only a small usage of refrigerants is necessary.

The gaseous hydrogen chloride preferably originates from the hydrolysis of organochlorosilanes A. The process is in principle applicable to all hydrolyses of organochlorosilanes A which produce gaseous hydrogen chloride.

The organochlorosilanes A preferably have the general formula I $$R_aSiCl_{4-a} \tag{I}$$

where
the radicals R are identical or different radicals selected from among hydrogen and unsubstituted and substituted C$_1$-C$_{18}$ hydrocarbon radicals and
a is 0, 1, 2 or 3,
with the proviso that at least 10 mol % of the radicals R are hydrocarbon radicals.

Examples of radicals R in the general formula (I) are alkyl radicals such as the methyl, ethyl, n-propyl, isopropyl, n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical; cycloalkyl radicals such as cyclopentyl, cyclohexyl, 4-ethylcyclohexyl, cycloheptyl, norbornyl radicals and methylcyclohexyl radicals; aryl radicals such as the phenyl, biphenylyl, and naphthyl radicals; alkaryl radicals such as the o-, m-, and p-tolyl radicals and ethylphenyl radicals; aralkyl radicals such as the benzyl radical and the alpha- and the β-phenylethyl radicals.

Examples of substituted radicals R are haloalkyl radicals such as the 3,3,3-trifluoro-n-propyl radical, the 2,2,2',2',2'-hexafluoroisopropyl radical and the heptafluoroisopropyl radical.

R preferably has from 1 to 6 carbon atoms. Particular preference is given to the methyl or phenyl radical.

Particular preference is given to hydrolyzing dimethyldichlorosilane, trimethylchlorosilane, methyltrichlorosilane and mixtures thereof. In particular, the gaseous hydrogen chloride originates from the hydrolysis of dimethyldichlorosilane. The contaminated gaseous hydrogen chloride is preferably scrubbed using the starting chlorosilane of the hydrolysis, i.e. organochlorosilane A and organochlorosilane B are identical.

Organochlorosilane B is most preferably dimethyldichlorosilane, trimethylchlorosilane, methyltrichlorosilane and mixtures thereof. In particular, organochlorosilane B is dimethyldichlorosilane.

Scrubbing is preferably carried out using at least 10 times, in particular 20 times, the stoichiometric amount of organochlorosilane B required for hydrolysis of the water of the contaminated gaseous hydrogen chloride. In this way, water is removed completely and relatively high-boiling oligomers are mostly removed.

The hydrogen chloride is saturated with the organochlorosilane B, according to pressure and temperature, after scrubbing with liquid organochlorosilane B. The advantage is that it is then simple to select a material for further processing steps since the hydrogen chloride is no longer corrosive and another advantage is that the organochlorosilanes A and B usually have very low melting points and for this reason icing does not have to be expected even at very low temperatures. For the preferred case of dimethyldichlorosilane, the melting point is −76° C. After this step, it is possible to use simple, metallic materials which are cheaper and also less sensitive to mechanical loading.

The scrubbing of the hydrogen chloride using organochlorosilane B is preferably carried out at temperatures of from 0° C. to 50° C., in particular from 10° C. to 30° C. The pressures are preferably from 1 to 20 bar, in particular from 2 to 10 bar.

The scrubbing of the hydrogen chloride using organochlorosilane B is preferably carried out in a scrubbing column. The scrubbing column preferably consists of glass, enameled metal or plastic.

In a preferred embodiment, the hydrogen chloride is scrubbed with liquid chloromethane after the scrub using organochlorosilane B. The now dry hydrogen chloride gas is cooled by the evaporation of the chloromethane. The temperature is preferably from −15° C. to −55° C., more preferably from −20° C. to −50° C. The pressures are preferably from 1 to 20 bar, in particular from 2 to 10 bar.

The silane constituents are condensed out upon cooling and can be recirculated to the first scrubber. The amount of chloromethane is preferably regulated so that a constant, desired temperature is achieved at the top of the scrubbing column. The purified hydrogen chloride contains chloromethane in accordance with the vapor pressure. However, since the hydrogen chloride is preferably used for preparing chloromethane, this constituent does not interfere in this further use and can therefore remain in the hydrogen chloride. The gaseous hydrogen chloride is preferably used as a raw material for the synthesis of chloromethane.

Scrubbing with chloromethane is preferably carried out using from a 0.05-fold to 1-fold, in particular from a 0.1-fold to 0.5-fold amount of chloromethane, in each case based on the mass of the gaseous hydrogen chloride.

The scrubbing of the hydrogen chloride using chloromethane is preferably carried out in a scrubbing column. The liquid chloromethane is preferably introduced into the scrubbing column in the upper third of the column. The scrubbing column can consist of metal, in particular steel.

All symbols above in the above formulae have their meanings independently of one another in each case. Unless indicated otherwise, all amounts and percentages are by weight, all pressures are 0.10 MPa (abs.) and all temperatures are 20° C.

EXAMPLE

The following measured values were determined by gas chromatography.

An HCl stream from a hydrolysis of dimethyldichlorosilane contains 0.15% of hexamethylcyclotetrasiloxane, 0.32% of octamethylcyclotetrasiloxane, 0.06% of decamethylcyclopentasiloxane, 0.15% of dichlorotetramethyldisiloxane and 0.5% of water.

In a first scrubber, 17 t/h of this contaminated HCl gas are introduced at 4 bar at the lower end and brought into contact with 500 kg of dimethyldichlorosilane introduced at the top; to this were added 1000 kg of bottoms from a chloromethane scrubber. Water and siloxanes are eliminated to below the detection limit.

The overhead product from the first scrubber is introduced into the chloromethane scrubber at the lower end, and 1000 kg/h of dimethyldichlorosilane go into the chloromethane scrubber at the top of which 2600 kg/h of liquid chloromethane are introduced. Temperatures of −44° C. at the top and −20° C. at the bottom are established. All of the dimethyldichlorosilane is separated off as bottoms in the chloromethane scrubber and recirculated to the first scrubber. The HCl gas which has been freed of siloxane components and is discharged at the top of the chloromethane scrubber is fed with a proportion of 2600 kg/h of chloromethane to a chloromethane synthesis.

The invention claimed is:

1. A process for purifying contaminated gaseous hydrogen chloride containing water, organochlorosilane A and/or hydrolysis products thereof, comprising scrubbing the contaminated gaseous hydrogen chloride with a liquid organochlorosilane B to form a partially decontaminated gaseous hydrogen chloride, and after the scrubbing with organochlorosilane B, scrubbing the partially decontaminated gaseous hydrogen chloride with liquid chloromethane, wherein organochlorosilanes A and B comprise organochlorosilanes of the formula $$R_a SiCl_{4-a} \quad (I)$$

where
the radicals R are identical or different radicals selected from among hydrogen and unsubstituted and substituted $C_1$-$C_{18}$ hydrocarbon radicals and
a is 0, 1, 2 or 3,
with the proviso that at least 10 mol % of the radicals R are hydrocarbon radicals.

2. The process of claim 1, wherein the gaseous hydrogen chloride originates from the hydrolysis of an organochlorosilane A.

3. The process of claim 1, wherein organochlorosilane A is selected from the group consisting of dimethyldichlorosilane, trimethylchlorosilane, methyltrichlorosilane and mixtures thereof.

4. The process of claim 1, wherein organochlorosilane A and organochlorosilane B are identical.

5. The process of claim 2, wherein organochlorosilane A and organochlorosilane B are identical.

6. The process of claim 3, wherein organochlorosilane A and organochlorosilane B are identical.

7. The process of claim 1, wherein at least 10 times the stoichiometric amount of organochlorosilane B required for hydrolyzing water contained in the contaminated gaseous hydrogen chloride is employed for scrubbing.

8. The process of claim 1, wherein scrubbing of the hydrogen chloride using organochlorosilane B is carried out at a temperature in the range of from 0° C. to 50° C.

9. The process of claim 1, wherein the temperature during scrubbing with liquid chloromethane is from −15° C. to −55° C.

10. The process of claim 1, wherein the purified hydrogen chloride is employed for preparing chloromethane.

11. The process of claim 1, wherein a purified, scrubbed gaseous HCl fraction from the second scrubbing with chloromethane is diluted with further chlormethane and input into a reactor for producing chloromethane.

* * * * *